US012687531B2

(12) United States Patent
Schaller et al.

(10) Patent No.: US 12,687,531 B2
(45) Date of Patent: Jul. 21, 2026

(54) HYDROGEN SENSOR WITH SORPTION ELEMENT FOR WATER VAPOR

(71) Applicant: Infineon Technologies AG, Neubiberg (DE)

(72) Inventors: Rainer Markus Schaller, Aichen (DE); Klaus Elian, Alteglofsheim (DE)

(73) Assignee: Infineon Technologies AG, Neubiberg (DE)

( * ) Notice: Subject to any disclaimer, the term of this patent is extended or adjusted under 35 U.S.C. 154(b) by 294 days.

(21) Appl. No.: 18/347,130

(22) Filed: Jul. 5, 2023

(65) Prior Publication Data

US 2024/0027412 A1    Jan. 25, 2024

(30) Foreign Application Priority Data

Jul. 20, 2022    (DE) .......................... 102022118113.8

(51) Int. Cl.
G01N 33/00 (2006.01)

(52) U.S. Cl.
CPC ....... G01N 33/0016 (2013.01); G01N 33/005 (2013.01)

(58) Field of Classification Search
CPC .......................... G01N 33/005; G01N 33/0016
See application file for complete search history.

(56) References Cited

U.S. PATENT DOCUMENTS

| | | | |
|---|---|---|---|
| 7,568,375 B2 | 8/2009 | Sasaki et al. | |
| 8,196,448 B2 | 6/2012 | Kuebel | |

| | | | | |
|---|---|---|---|---|
| 2006/0048562 A1 | 3/2006 | Oishi et al. | | |
| 2006/0219552 A1 | 10/2006 | Sasaki et al. | | |
| 2021/0356348 A1 * | 11/2021 | Solomon | .............. | G01M 3/205 |

FOREIGN PATENT DOCUMENTS

| | | | | | |
|---|---|---|---|---|---|
| CN | 1908641 A | 2/2007 | | | |
| CN | 102192930 A | 9/2011 | | | |
| CN | 109954481 A | 7/2019 | | | |
| DE | 102013007872 B4 * | 1/2015 | ............. | G01N 27/40 | |
| DE | 102017215312 A1 | 3/2019 | | | |
| EP | 3076146 A1 | 10/2016 | | | |
| JP | 2010002193 A | 1/2010 | | | |
| JP | 2010002197 A | 1/2010 | | | |
| JP | 2010091305 A * | 4/2010 | | | |
| JP | 6995003 B2 * | 2/2022 | | | |
| KR | 20070083478 A | 8/2007 | | | |

OTHER PUBLICATIONS

Machine translation of DE 102013007872 A1 (Year: 2013).*
Machine translation of JP 2010091305 A (Year: 2010).*
Machine translation of JP 6995003 B2 (Year: 2022).*

* cited by examiner

*Primary Examiner* — Nathaniel J Kolb
(74) *Attorney, Agent, or Firm* — Harrity & Harrity, LLP

(57) ABSTRACT

What is disclosed is a hydrogen sensor (100) having a housing (101) that includes a cavity (102) and has a passage opening (103) from the cavity (102) to a gas connection of the hydrogen sensor (100) or an environment, having a first hydrogen sensor element (104), disposed in the cavity (102), for measurement of a hydrogen content in the cavity (102), having a first sorption element (105) for sorption of water and/or water vapor, especially an adsorption element (105) for adsorption of water and/or water vapor, and having a first heater (106) for bakeout of the first sorption element (105), wherein the first sorption element (105) has open pores and is disposed in the passage opening (103).

22 Claims, 8 Drawing Sheets

HYDROGEN SENSOR WITH SORPTION ELEMENT FOR WATER VAPOR

CROSS REFERENCE TO RELATED APPLICATION

This application claims priority to German Patent Application No. 102022118113.8 filed on Jul. 20, 2022, the content of which is incorporated by reference herein in its entirety.

FIELD

The present disclosure relates to a hydrogen sensor.

BACKGROUND

Fossil energy sources are increasingly being replaced by environmentally friendly fuels that are also referred to as "green fuel". For example, hydrogen generated with the aid of wind turbines, which is also referred to as green hydrogen, is being used as an energy source to drive motor vehicles. In particular, fuel cells are used in order to use the green hydrogen to produce power again for drive motors. In this connection, there is a need for sensors in order to be able to determine the hydrogen content in gas-conducting conduits. There is likewise a need for sensors with which hydrogen gas that escapes in an unwanted manner, which can lead to creation of explosive hydrogen/oxygen gas mixtures, can be detected.

US 2006/219552 A1 describes a gas sensor. The known gas sensor includes walls that bound detection of gas and have an introduction opening through which a gas to be observed is introduced into the gas detection chamber. The known gas sensor further includes a measuring element which is disposed in the gas detection chamber and measures the concentration of a subject gas present in the gas to be observed. Likewise provided is a heating element that forms at least a portion of the walls, wherein the portion faces the gas detection chamber. The heating element is disposed opposite the gas detection chamber. The known gas sensor further includes a first demoisturizer that absorbs water in a reversible manner and is disposed on a portion of the walls, and which is disposed opposite the introduction opening in relation to the measuring element.

There is a need for a hydrogen sensor with which a hydrogen content can be determined with higher operational reliability.

SUMMARY

From this starting point, a hydrogen sensor according to the main claim is proposed. Advantageous configurations are specified in the subsidiary claims.

What is proposed is a hydrogen sensor having a housing that includes a cavity and has a passage opening from the cavity to a gas connection of the hydrogen sensor or an environment, having a first hydrogen sensor element, disposed in the cavity, for measurement of a hydrogen content in the cavity, having a first sorption element for sorption of water and/or water vapor, and having a first heater for bakeout of the first sorption element, wherein the first sorption element has open pores and is disposed in the passage opening.

The first sorption element may especially be an absorption element for absorption of water and/or water vapor. The first sorption element is disposed in the passage opening such that it closes the passage opening as completely as possible. Transport of gas from the environment or a gas connection of the hydrogen sensor to the cavity is preferably possible only through the pores of the first sorption element.

The proposed hydrogen sensor largely prevents any influence on the hydrogen sensor element by water and/or water vapor entering the cavity. In particular, water and water vapor can be more reliably bound by the sorption element.

In working examples, a pore size of the first sorption element is less than 1 mm, especially less than 10 μm, preferably less than 1 μm. The smaller the pore size, the greater the certainty of achieving ingress only of the hydrogen into the cavity.

In working examples, the first sorption element is a sorption element made of zeolite. Zeolite has good processability. In addition, it can be heated easily, which means that sorbed water or sorbed water vapor can be released again. Thus, regeneration of the sorption element is possible in a simple manner.

Further working examples envisage covering of the passage opening by a gas-permeable membrane. In this way, it is possible to prevent unwanted extraneous particles from getting into or onto the sorption element.

The hydrogen sensor may further include a temperature sensor element. The temperature sensor element can, for example, control the first heater. In particular, the temperature sensor element can enable more exact measurement by the hydrogen sensor element.

In further configurations, the hydrogen sensor may have a second hydrogen sensor element, a second sorption element and a second heater for bakeout of the second absorption element, where the hydrogen sensor has a switch for alternate heating of the first heater and the second heater. In particular, the hydrogen sensor in this case may be operated alternately with the first hydrogen sensor element and the second hydrogen sensor element. One of the sorption elements in this case can be regenerated, and the other sorption element can bind water or water vapor in the measuring hydrogen sensor element.

In working examples, it may be the case that the first heater is the first hydrogen sensor element. In other words, by actuating the first hydrogen sensor element, it can be heated to such an extent that the heat generated can regenerate the first sorption element.

The hydrogen sensor may especially include a lead frame or a printed circuit board. The first heater and/or the first sorption element may be disposed on the lead frame or the printed circuit board. This can simplify the production of the hydrogen sensor.

The first heater may especially be formed in the lead frame or the printed circuit board. In this way, there is no need to provide an additional separate heater.

In variants, it may be the case that the passage opening leads to a change in a flow direction from the environment or in the gas connection to the cavity of more than 80°, especially more than 160°. In this way, it is possible to reduce the risk that the hydrogen sensor element is enveloped solely by a laminar flow and leads to an inaccurate measurement result.

BRIEF DESCRIPTION OF THE DRAWINGS

Examples of the hydrogen sensor are now described in detail with reference to the figures. The figures illustrate:

FIG. 3: a hydrogen sensor;

FIG. 4: a hydrogen sensor;

FIG. 5: a hydrogen sensor;

FIG. 6: a hydrogen sensor;

FIG. 7: a hydrogen sensor; and

FIG. 8: a hydrogen sensor.

DETAILED DESCRIPTION

Figure 1:
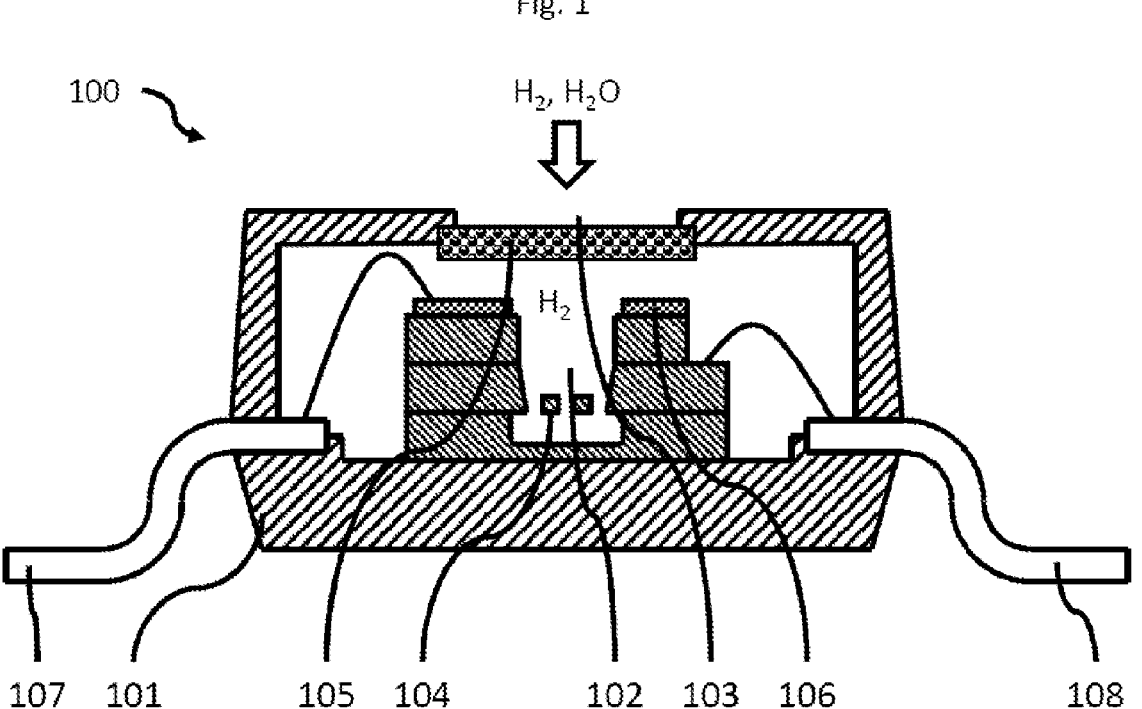
FIG. 1: a hydrogen sensor.

The hydrogen sensor 100 shown in FIG. 1 has a housing 101. A cavity 102 is provided in the housing. A passage opening 103 leads from the cavity 102 to a gas connection (not shown) of the hydrogen sensor 100 or to the environment. Disposed in the cavity 102 is a first hydrogen sensor element 104 for measuring a hydrogen content in the cavity 102. Also provided is a first sorption element 105 for sorption of water and/or water vapor. The first sorption element has open pores. The first sorption element is disposed in the passage opening 103. The sorption element may consequently, as indicated in FIG. 1, have the effect that only the hydrogen can pass through the first sorption element 105.

The pore size of the first sorption element 105 may especially be less than 1 mm, preferably less than 10 μm, especially preferably less than 1 μm.

In the working example shown, the first sorption element 105 includes zeolite. This material has been found to be particularly suitable for the sorption of water and/or water vapor.

The hydrogen sensor 100 further includes a temperature sensor element (not shown here).

The hydrogen sensor 100 likewise has a lead frame 107, 108. This permits the connection to the first heater 106, and also to the hydrogen sensor element 104 and the temperature sensor element, as shown by bonding wires.

Figure 2:
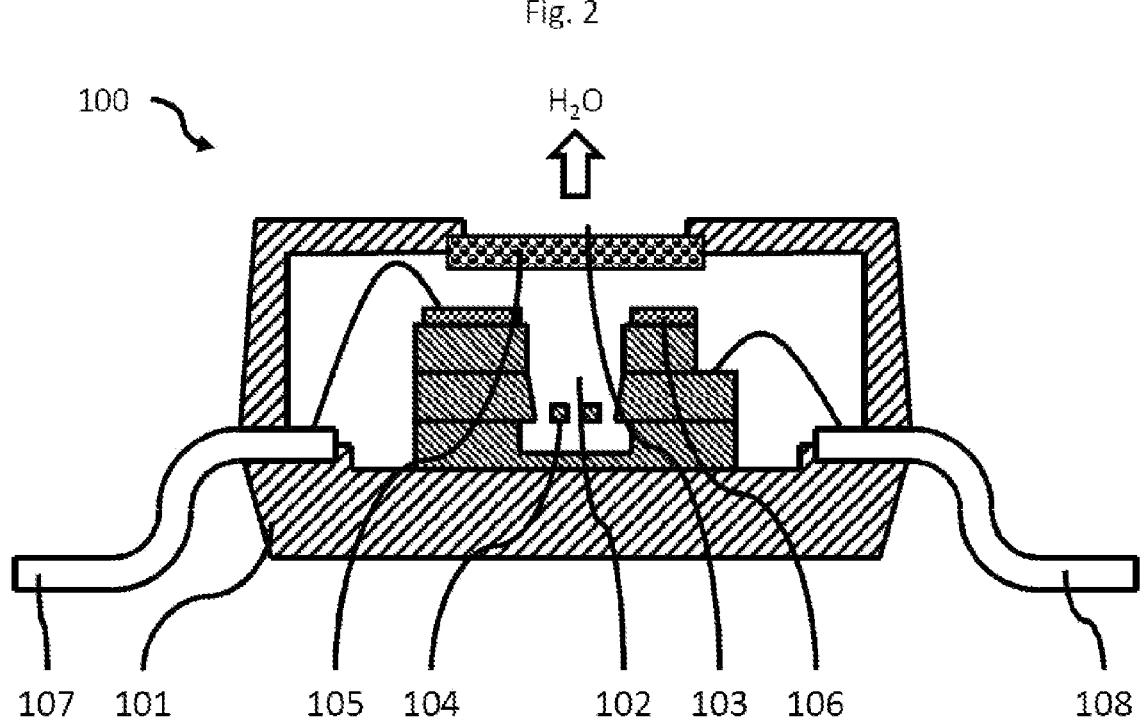
FIG. 2: the hydrogen sensor shown in FIG. 1.

FIG. 2 shows the hydrogen sensor 100 when the heater 106 is being used to regenerate the first sorption element 105. It is indicated that the water vapor or the water is driven out of the sorption element 105 and/or the cavity 102.

Figure 3:
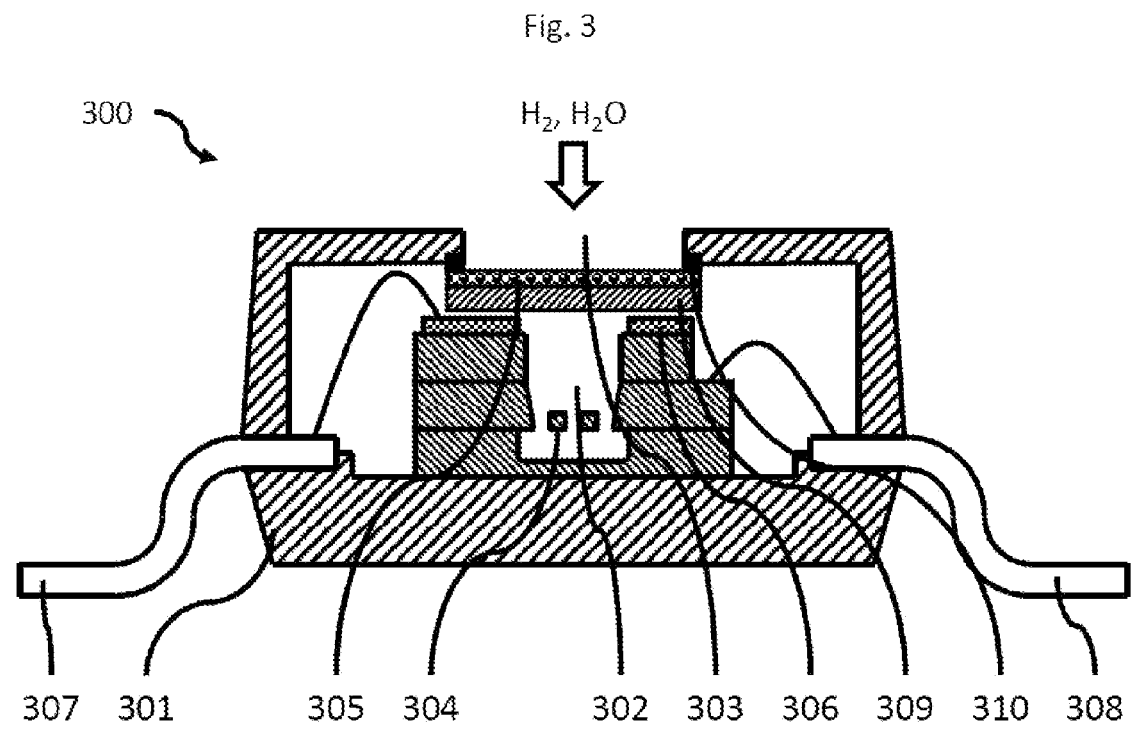

FIG. 3 shows a further hydrogen sensor 300. The hydrogen sensor 300 again has a housing 301 that includes a cavity 302 and includes a passage opening 303 from the cavity 302 to a gas connection of the hydrogen sensor 300 or an environment.

Further provided in the cavity 302 is a first hydrogen sensor element 304 for measurement of a hydrogen content in the cavity 302. Also provided is a first sorption element 305 with which water and/or water vapor can be sorbed, in order that it does not get into the cavity 302. The sorption element 305 is disposed here on a carrier 309 and is sealed with respect to the housing 301 by a seal 310.

A first heater 306 may, as elucidated in relation to FIG. 1 and FIG. 2, be used for bakeout of the first sorption element 305. The first sorption element 305 has open pores, such that gas can escape through the sorption element to the left and right and can then get into the cavity 302.

Figure 4:
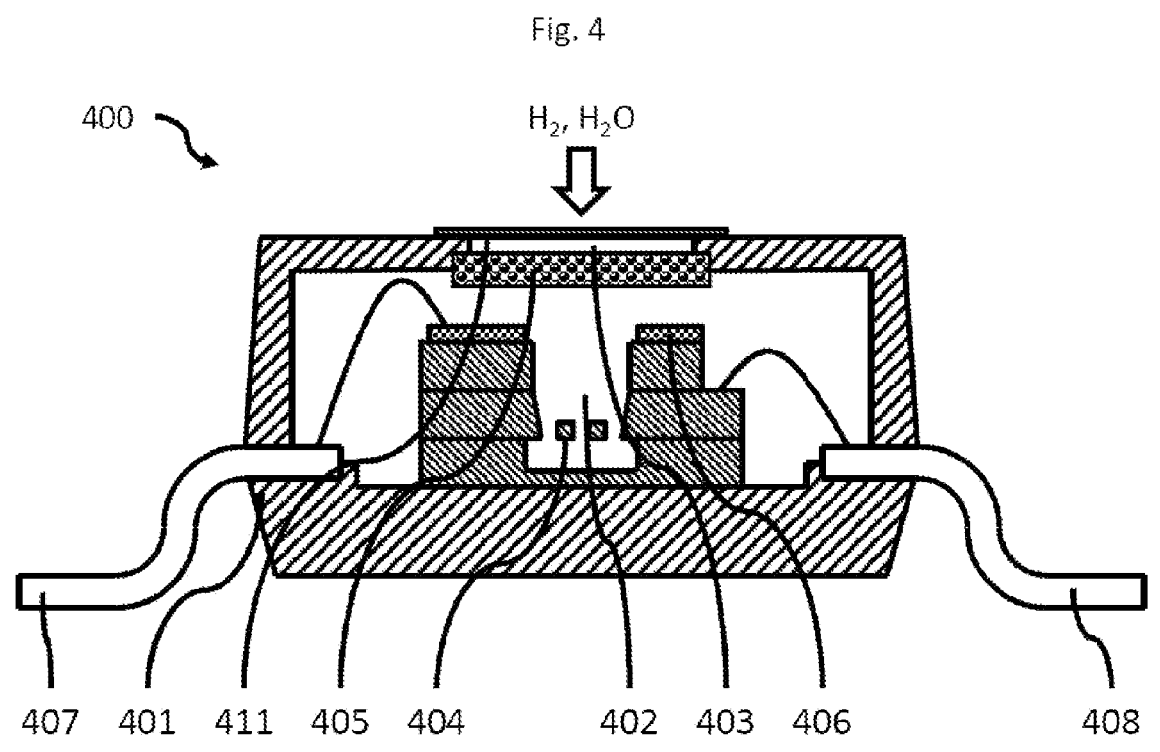

FIG. 4 shows a hydrogen sensor 400 having a housing 401 which includes a cavity 402 and has a passage opening 403 from the cavity 402 to a gas connection of the hydrogen sensor 400 or an environment.

The hydrogen sensor 400 is provided with a first hydrogen sensor element 404, disposed in the cavity 402, for measuring a hydrogen content in the cavity 402, a first sorption element 405 for sorption of water and/or water vapor, and a first heater 406 for bakeout of the first sorption element 405. The first sorption element 405 has open pores and is disposed in the passage opening 403.

Moreover, the passage opening 403 is covered by a gas-permeable membrane 411, such that relatively large particles cannot get to the sorption element 405, and so it is better protected.

The electrical components may be electrically connected here by a lead frame 407, 408 in order that the hydrogen sensor 400 can be read.

Figure 5:
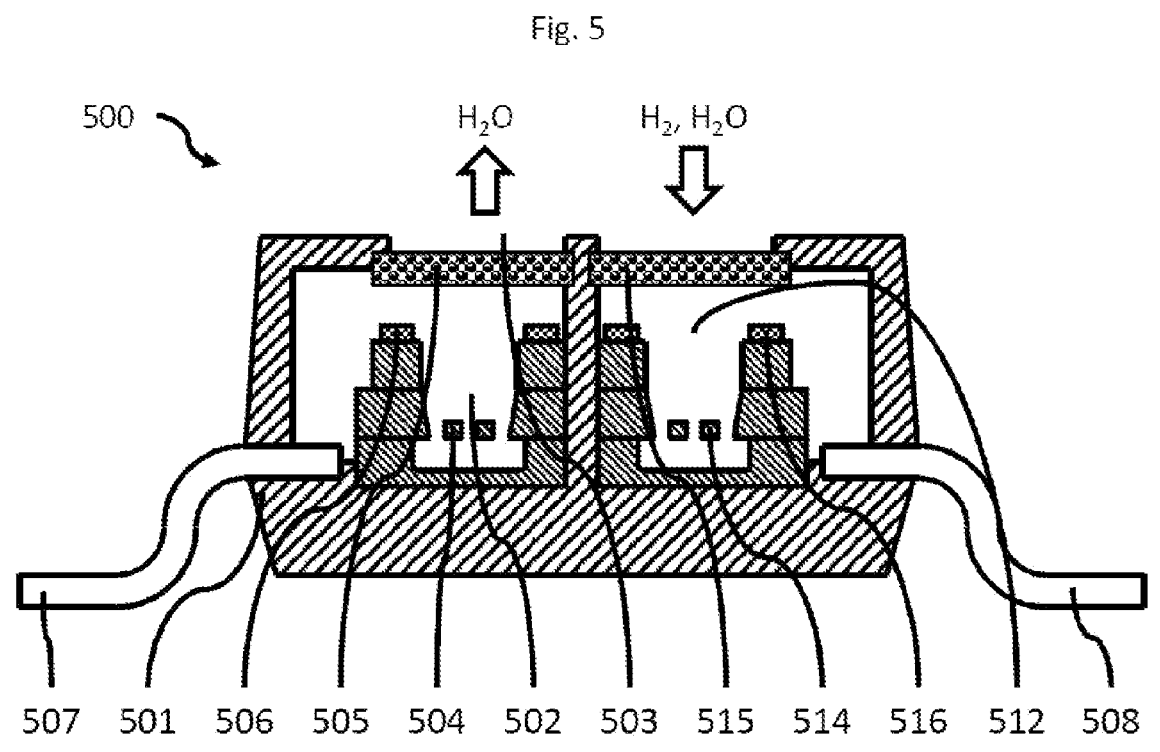

FIG. 5 shows a hydrogen sensor 500 having a housing 501 which includes a cavity 502 and has a passage opening 503 from the cavity 502 to a gas connection of the hydrogen sensor 500 or an environment, having a first hydrogen sensor element 504, disposed in the cavity 502, for measuring a hydrogen content in the cavity 502, having a first sorption element 505 for sorption of water and/or water vapor, and having a first heater 506 for bakeout of the first sorption element 505.

Moreover, the hydrogen sensor 500 has a second hydrogen sensor element 514, a second sorption element 515 and a second heater 516 for bakeout of the second sorption element 515. The second hydrogen sensor element 514 is disposed here in a second cavity 512. The construction of the hydrogen sensor 500 can especially be mirror-symmetric. The hydrogen sensor 500 may have a switch for alternate heating of the first heater 506 and the second heater 516. In this way, it is possible to regenerate the first sorption element 505 while the second hydrogen sensor element 514 is being used for measurement. Alternatively, the second sorption element 515 can be regenerated when the first hydrogen sensor element 504 is being used for measurement. Consequently, the hydrogen sensor 500 can enable continuous measurement of the hydrogen content.

Using contacts formed on the lead frame 507, 508, it is possible to read and control the hydrogen sensor 500.

Figure 6:
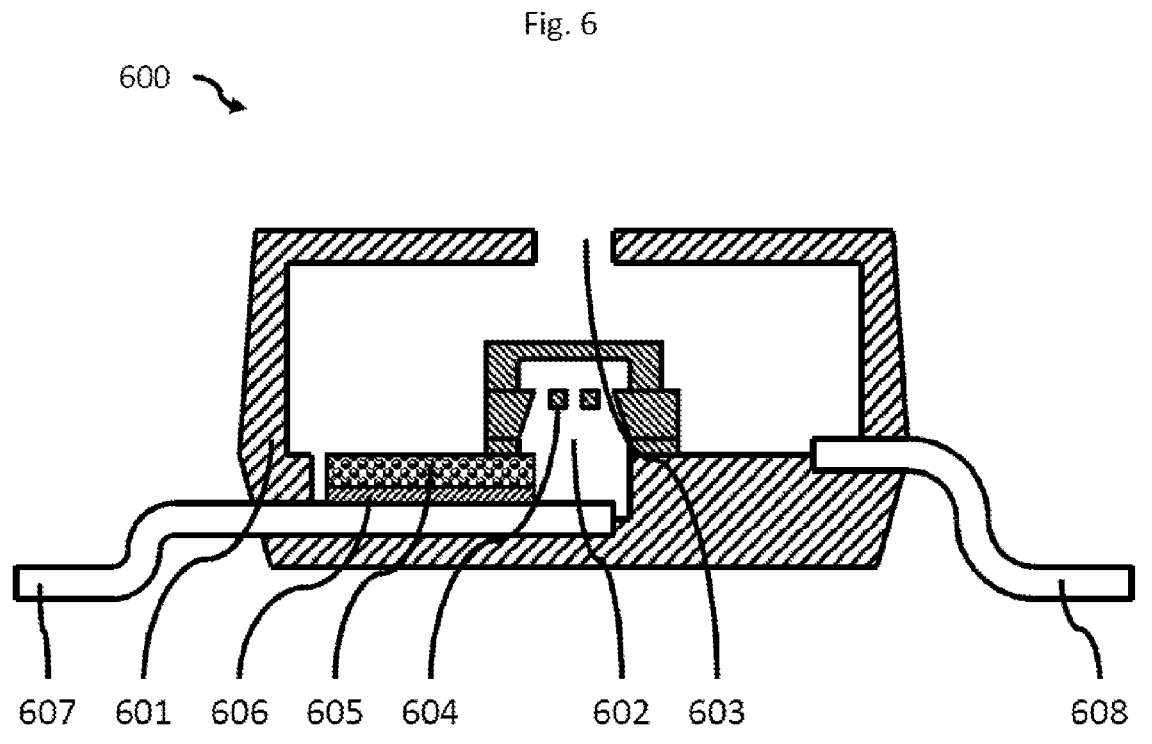

FIG. 6 shows a further example of a hydrogen sensor 600. The hydrogen sensor 600 in turn has a housing 601 having a cavity 602 and a passage opening 603. Disposed in the cavity 602 is a first hydrogen sensor element 604. A heater 606 is disposed immediately above and is supported by the lead frame 607. Atop the heater 606 is a first sorption element 605. Gas to be analyzed passes in turn through the passage opening 603 via the first sorption element 605 into the cavity 602, with sorption of any water vapor present in the analysis gas.

The connecting wires to the contacts of the lead frame 607, 608 are not shown for simplification.

Figure 7:
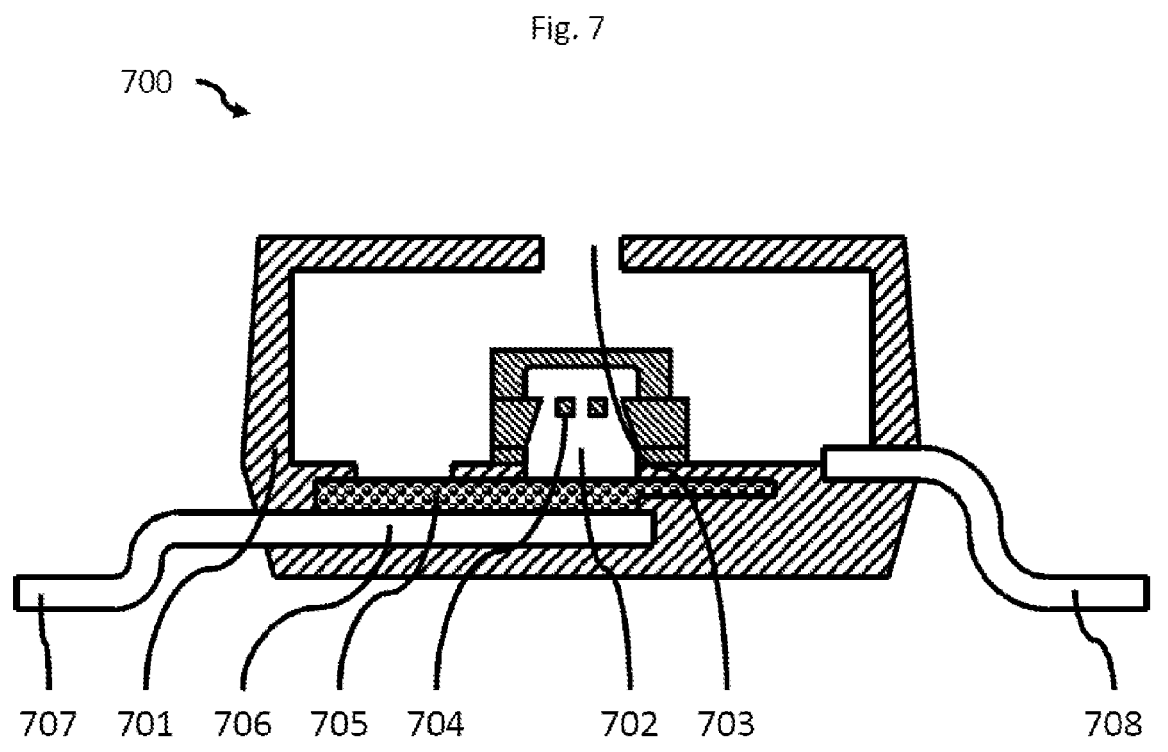

FIG. 7 shows a further hydrogen sensor 700. The elements 707, 701, 705, 704, 702, 703 and 708 correspond in terms of their function to the elements 607, 601, 605, 604, 602, 603 and 608, as shown in FIG. 6. By contrast with the hydrogen sensor 600, the first sorption element 705 in the hydrogen sensor 700 is embedded in the housing 701. Moreover, the first heater 706 for bakeout of the first sorption element 705 is configured as part of the lead frame 707.

Figure 8:
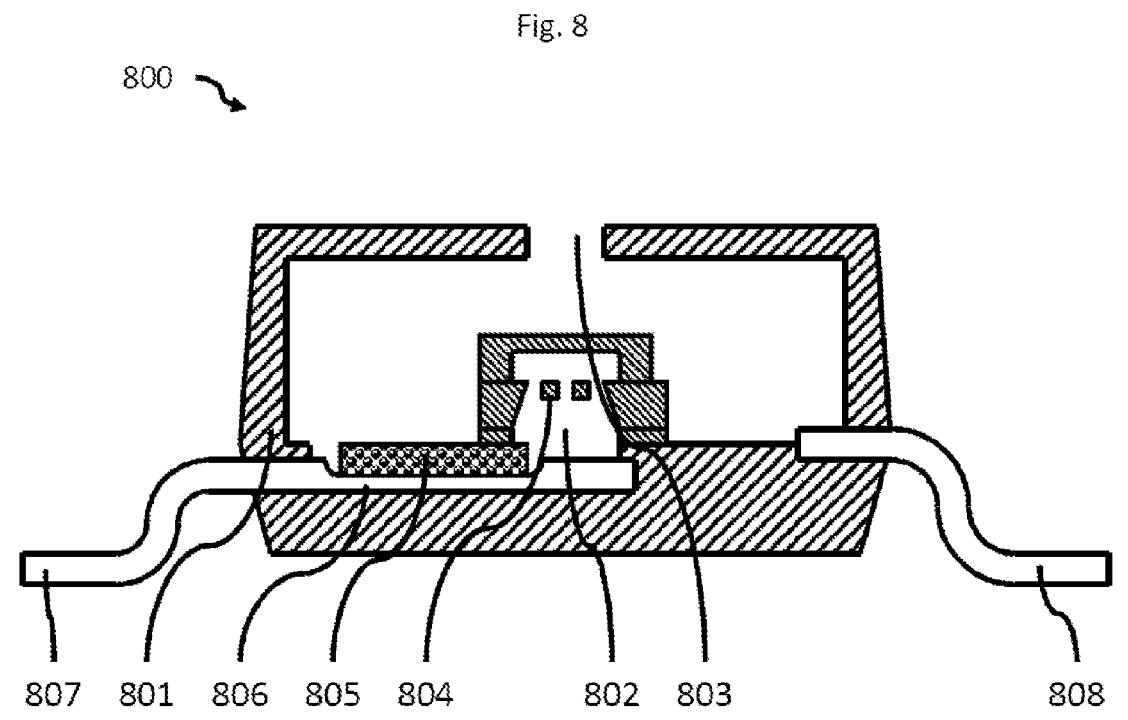

Finally, FIG. 8 also shows a hydrogen sensor 800. The elements 807, 801, 806, 805, 804, 802, 803 and 808 correspond to the elements 707, 701, 706, 705, 704, 702, 703 and 708 of the hydrogen sensor 700 shown in FIG. 7. However, in the present case, the first sorption element 805 is supported directly by the lead frame 807 and is not embedded directly in the housing 81.

Aspects

Some working aspects are defined by the aspects that follow:

Aspect 1. A hydrogen sensor (100) having a housing (101) that includes a cavity (102) and has a passage opening (103) from the cavity (102) to a gas connection of the hydrogen sensor (100) or an environment, having a first hydrogen sensor element (104), disposed in the cavity (102), for measurement of a hydrogen content in the cavity (102), having a first sorption element (105) for sorption of water and/or water vapor, especially an adsorption element (105) for adsorption of water and/or water vapor, and having a first heater (106) for bakeout of the first sorption element (105), characterized in that the first sorption element (105) has open pores and is disposed in the passage opening (103).

Aspect 2. The hydrogen sensor (100) according to aspect 1, wherein a pore size of the first sorption element (105) is less than 1 mm, especially less than 10 μm, especially less than 1 μm.

Aspect 3. The hydrogen sensor (100) according to aspect 1 or 2, wherein the first sorption element (105) includes zeolite.

Aspect 4. The hydrogen sensor (400) according to any of aspects 1 to 3, wherein the passage opening (103) has been covered by a gas-permeable membrane (411).

Aspect 5. The hydrogen sensor (100) according to any of aspects 1 to 4, wherein the hydrogen sensor (100) includes a temperature sensor element.

Aspect 6. The hydrogen sensor (500) according to any of aspects 1 to 5, having a second hydrogen sensor element (514), having a second sorption element (515), and having a second heater (516) for bakeout of the second sorption element (515), wherein the hydrogen sensor (500) has a switch for alternate heating of the first heater (506) and the second heater (516).

Aspect 7. The hydrogen sensor (100) according to any of aspects 1 to 6, wherein the first heater (106) is the first hydrogen sensor element (514).

Aspect 8. The hydrogen sensor (100) according to any of aspects 1 to 7, wherein the hydrogen sensor (100) includes a lead frame (107, 108) or a printed circuit board.

Aspect 9. The hydrogen sensor (600) according to aspect 8, wherein the first heater (606) and/or the first sorption element (606) is disposed on the lead frame (607) or the printed circuit board.

Aspect 10. The hydrogen sensor (700) according to aspect 8 or 9, wherein the first heater (706) is formed in the lead frame (707) or the printed circuit board.

Aspect 11. The hydrogen sensor (700) according to any of aspects 1 to 10, wherein the passage opening (703) leads to a change in a direction of flow from the environment to the cavity (702) of more than 80°, especially more than 160°.

Although this description illustrated and described specific working aspects, persons of average skill in the art will see that a multitude of alternative and/or equivalent implementation may be chosen as a substitution for the specific working aspects that are disclosed and described in this description, without departing from the scope of the implementation disclosed. It is the intention that this application covers all adaptations or variations of the specific working aspects that are discussed here. It is therefore intended that this implementation is restricted solely by the claims and the equivalents of the claims.

The invention claimed is:

1. A hydrogen sensor, comprising:

a housing that comprises a passage opening from a gas connection of the hydrogen sensor or an environment to an outer cavity;

a hydrogen sensor element, arranged in an inner cavity, configured to measure a hydrogen content in the inner cavity;

a sorption element for sorption of at least one of water or water vapor, wherein the sorption element has open pores and is arranged within the housing between the outer cavity and the inner cavity, wherein the inner cavity has an inner cavity opening that faces away from the passage opening; and a heater for bakeout of the sorption element, wherein the sorption element is disposed atop the heater.

2. The hydrogen sensor as claimed in claim 1, wherein a pore size of the sorption element is less than 1 mm.

3. The hydrogen sensor as claimed in claim 1, wherein the sorption element comprises zeolite.

4. The hydrogen sensor as claimed in claim 1, further including:

a gas-permeable membrane that covers the passage opening.

5. The hydrogen sensor as claimed in claim 1, wherein the hydrogen sensor comprises a temperature sensor element.

6. The hydrogen sensor as claimed in claim 1, further comprising:

a lead frame or a printed circuit board.

7. The hydrogen sensor as claimed in claim 6, wherein the heater or the sorption element is arranged on the lead frame or the printed circuit board.

8. The hydrogen sensor as claimed in claim 6, wherein the heater is formed in the lead frame or the printed circuit board.

9. The hydrogen sensor as claimed in claim 1, wherein an arrangement of the passage opening, the sorption element, and the inner cavity opening leads to a change in a direction of flow from the gas connection or the environment to the inner cavity of more than 80°.

10. The hydrogen sensor as claimed in claim 9, wherein an arrangement of the passage opening, the sorption element, and the inner cavity opening leads to a change in a direction of flow from the gas connection or the environment to the inner cavity of more than 160°.

11. The hydrogen sensor as claimed in claim 1, wherein the sorption element is an adsorption element for adsorption of at least one of the water or the water vapor.

12. The hydrogen sensor as claimed in claim 1, wherein a pore size of the sorption element is less than 1 μm.

13. The hydrogen sensor as claimed in claim 1, further comprising:

a lead frame that extends into the housing, wherein the heater is arranged on the lead frame in direct contact with the lead frame.

14. The hydrogen sensor as claimed in claim 13, wherein the lead frame and the passage opening are arranged at opposite sides of the housing.

15. The hydrogen sensor as claimed in claim 13, wherein the sorption element is arranged on the heater such that the heater is arranged between the lead frame and the sorption element.

16. The hydrogen sensor as claimed in claim 15, wherein the sorption element is in direct contact with the heater.

17. The hydrogen sensor as claimed in claim 13, wherein the passage opening, the sorption element, and the inner cavity opening are arranged such that a position of the sorption element relative to the passage opening and the inner cavity opening is configured to cause a change in a direction of flow from the passage opening to the inner cavity of more than 80°.

18. The hydrogen sensor as claimed in claim 13, wherein the passage opening, the sorption element, and the inner cavity opening are arranged such that a position of the sorption element relative to the passage opening and the inner cavity opening is configured to cause a change in a direction of flow from the passage opening to the inner cavity of more than 160°.

19. The hydrogen sensor as claimed in claim 1, further comprising:

a lead frame that extends into the housing, wherein the sorption element is arranged on the lead frame in direct contact with the lead frame, and wherein the heater is integral with the lead frame.

20. The hydrogen sensor as claimed in claim 19, wherein the lead frame and the passage opening are arranged at opposite sides of the housing, and wherein the sorption element is arranged at the inner cavity opening.

21. The hydrogen sensor as claimed in claim 1, wherein the inner cavity is defined by a stacked structure arranged within the outer cavity.

22. A hydrogen sensor, comprising:

a housing that has a passage opening from a gas connection of the hydrogen sensor or an environment to an outer cavity;

a hydrogen sensor element, arranged in an inner cavity, configured to measure a hydrogen content in the inner cavity;

a sorption element for sorption of at least one of water or water vapor, wherein the sorption element has open pores and is arranged within the housing between the outer cavity and the inner cavity, wherein the inner cavity has an inner cavity opening that faces away from the passage opening; and a heater for bakeout of the sorption element, wherein the sorption element is disposed in direct contact with the heater.

* * * * *